(12) United States Patent
Schneider et al.

(10) Patent No.: US 12,165,754 B2
(45) Date of Patent: Dec. 10, 2024

(54) SYSTEMS AND METHODS FOR IMPROVED OPTICAL CHARACTER RECOGNITION OF HEALTH RECORDS

(71) Applicant: Apixio, LLC, San Mateo, CA (US)

(72) Inventors: John O. Schneider, Los Gatos, CA (US); Vishnuvyas Sethumadhavan, Mountain View, CA (US); Haoning Fu, Belmont, CA (US)

(73) Assignee: APIXIO, LLC, San Mateo, CA (US)

( * ) Notice: Subject to any disclaimer, the term of this patent is extended or adjusted under 35 U.S.C. 154(b) by 0 days.

(21) Appl. No.: 18/176,202

(22) Filed: Feb. 28, 2023

(65) Prior Publication Data

US 2023/0207082 A1   Jun. 29, 2023

Related U.S. Application Data

(63) Continuation of application No. 15/662,246, filed on Jul. 27, 2017, now Pat. No. 11,610,653, which is a
(Continued)

(51) Int. Cl.
  *G16H 10/60* (2018.01)
  *G06F 16/583* (2019.01)
  (Continued)

(52) U.S. Cl.
  CPC ......... *G16H 10/60* (2018.01); *G06F 16/5846* (2019.01); *G06Q 10/0639* (2013.01);
  (Continued)

(58) Field of Classification Search
  CPC ............ G06F 16/5846; G06Q 10/0639; G06Q 10/10; G06Q 50/22; G06V 30/10;
  (Continued)

(56) References Cited

U.S. PATENT DOCUMENTS 5,164,899 A   11/1992   Sobotka
5,307,262 A   4/1994   Ertel
(Continued)

FOREIGN PATENT DOCUMENTS

CA   2216681 A1   3/1998
CA   2722773 A1   11/2009
(Continued)

OTHER PUBLICATIONS

A Lynunn, How Elasticsearch calculates significant terms, Jun. 10, 2015, ComperioSearch (Year: 2015).
(Continued)

*Primary Examiner* — Zhiyu Lu
(74) *Attorney, Agent, or Firm* — Armstrong Teasdale LLP

(57) ABSTRACT

Systems and methods to improve the optical character recognition of records, and in particular health records, are provided. An image of a medical record is received, and an initial optical image recognition (OCR) on the image is performed to identify text information. The OCR signal quality may be measured, and areas of insufficient OCR signal quality may be isolated. The signal quality is determined by a weighted average of semantic analysis of the resulting text, and/or OCR accuracy measures. The OCR process may be repeated on the isolated regions of lower signal quality, each time using a different OCR transform, until all regions are completed with a desired degree of signal quality (accuracy). All the regions of the document may then be recompiled into a single document for outputting.

18 Claims, 10 Drawing Sheets

Related U.S. Application Data continuation-in-part of application No. 13/223,228, filed on Aug. 31, 2011, now Pat. No. 10,176,541, and a continuation-in-part of application No. 13/747,336, filed on Jan. 22, 2013, now abandoned.

(60) Provisional application No. 62/369,007, filed on Jul. 29, 2016, provisional application No. 61/590,330, filed on Jan. 24, 2012, provisional application No. 61/379,228, filed on Sep. 1, 2010.

(51) Int. Cl.
    *G06Q 10/0639*     (2023.01)
    *G06Q 10/10*     (2023.01)
    *G06Q 50/22*     (2018.01)
    *G16H 30/20*     (2018.01)
    *G16H 40/63*     (2018.01)
    *G16H 40/67*     (2018.01)
    *G06V 30/10*     (2022.01)

(52) U.S. Cl.
    CPC .............. *G06Q 10/10* (2013.01); *G06Q 50/22* (2013.01); *G16H 30/20* (2018.01); *G16H 40/63* (2018.01); *G16H 40/67* (2018.01); *G06V 30/10* (2022.01)

(58) Field of Classification Search
    CPC ........ G16H 10/60; G16H 30/20; G16H 40/63; G16H 40/67; G16H 70/00; G16Z 99/00
    See application file for complete search history.

(56) References Cited

U.S. PATENT DOCUMENTS

| | | |
|---|---|---|
| 5,544,044 A | 8/1996 | Leatherman |
| 5,875,263 A | 2/1999 | Froessl |
| 5,924,074 A | 7/1999 | Evans |
| 6,076,088 A | 6/2000 | Paik |
| 6,151,581 A | 11/2000 | Kraftson |
| 6,209,095 B1 | 3/2001 | Anderson |
| 6,266,645 B1 | 7/2001 | Simpson |
| 6,336,108 B1 | 1/2002 | Thiesson |
| 6,341,265 B1 | 1/2002 | Provost |
| 6,505,196 B2 | 1/2003 | Drucker |
| 6,577,755 B1 | 6/2003 | Lorie |
| 6,601,055 B1 | 7/2003 | Roberts |
| 6,675,044 B2 | 1/2004 | Chen |
| 6,874,085 B1 | 3/2005 | Koo |
| 7,321,861 B1 | 1/2008 | Oon |
| 7,702,524 B1 | 4/2010 | Whibbs |
| 7,925,678 B2 | 4/2011 | Botros |
| 8,254,681 B1 | 8/2012 | Poncin |
| 8,380,530 B2 | 2/2013 | Marshall |
| 8,620,078 B1 | 12/2013 | Chapleau |
| 8,977,076 B2 | 3/2015 | Samadani |
| 9,495,515 B1 | 11/2016 | Kennedy |
| 10,628,553 B1 | 4/2020 | Murrish |
| 2001/0042080 A1 | 11/2001 | Ross |
| 2002/0007284 A1 | 1/2002 | Schurenberg |
| 2002/0010679 A1 | 1/2002 | Felsher |
| 2002/0103834 A1 | 8/2002 | Thompson |
| 2002/0120466 A1 | 8/2002 | Finn |
| 2002/0143562 A1 | 10/2002 | Lawrence |
| 2002/0188182 A1 | 12/2002 | Haines |
| 2003/0004748 A1 | 1/2003 | Coleman |
| 2003/0046280 A1 | 3/2003 | Rotter |
| 2003/0084043 A1 | 5/2003 | Acharya |
| 2003/0120458 A1 | 6/2003 | Rao |
| 2003/0120640 A1 | 6/2003 | Ohta |
| 2003/0187950 A1 | 10/2003 | Rising |
| 2003/0220915 A1 | 11/2003 | Fagan |
| 2003/0229510 A1 | 12/2003 | Kerr |
| 2004/0073458 A1 | 4/2004 | Jensen |
| 2004/0076264 A1 | 4/2004 | Sorenson |
| 2004/0109028 A1 | 6/2004 | Stern |
| 2004/0122702 A1 | 6/2004 | Sabol |
| 2004/0172297 A1 | 9/2004 | Rao |
| 2004/0220895 A1 | 11/2004 | Carus |
| 2004/0249667 A1 | 12/2004 | Oon |
| 2005/0043986 A1 | 2/2005 | McConnell |
| 2005/0137912 A1 | 6/2005 | Rao |
| 2005/0138017 A1 | 6/2005 | Keen |
| 2005/0154690 A1 | 7/2005 | Nitta |
| 2005/0182659 A1 | 8/2005 | Huttin |
| 2005/0192792 A1 | 9/2005 | Carus |
| 2005/0203773 A1 | 9/2005 | Soto |
| 2005/0228593 A1 | 10/2005 | Jones |
| 2005/0240439 A1 | 10/2005 | Covit |
| 2005/0251422 A1 | 11/2005 | Wolfman |
| 2005/0283062 A1 | 12/2005 | Hoffman |
| 2006/0026036 A1 | 2/2006 | Mahmood |
| 2006/0026525 A1 | 2/2006 | Fischer |
| 2006/0036619 A1 | 2/2006 | Fuerst |
| 2006/0047669 A1 | 3/2006 | Durrence |
| 2006/0053098 A1 | 3/2006 | Gardner |
| 2006/0112050 A1 | 5/2006 | Miikkulainen |
| 2006/0129435 A1 | 6/2006 | Smitherman |
| 2006/0179016 A1 | 8/2006 | Forman |
| 2006/0184475 A1 | 8/2006 | Krishnan |
| 2006/0241978 A1 | 10/2006 | Yoshii |
| 2006/0265249 A1 | 11/2006 | Follis |
| 2006/0265251 A1 | 11/2006 | Patterson |
| 2006/0265253 A1 | 11/2006 | Rao |
| 2007/0016450 A1 | 1/2007 | Bhora |
| 2007/0055545 A1 | 3/2007 | Maughan |
| 2007/0055552 A1 | 3/2007 | St. Clair |
| 2007/0061348 A1 | 3/2007 | Holland |
| 2007/0061393 A1 | 3/2007 | Moore |
| 2007/0078680 A1 | 4/2007 | Wennberg |
| 2007/0083390 A1 | 4/2007 | Gorup |
| 2007/0088559 A1 | 4/2007 | Kim |
| 2007/0106754 A1 | 5/2007 | Moore |
| 2007/0118399 A1 | 5/2007 | Avinash |
| 2007/0162308 A1 | 7/2007 | Peters |
| 2007/0168461 A1 | 7/2007 | Moore |
| 2007/0192143 A1 | 8/2007 | Krishnan |
| 2007/0219829 A1 | 9/2007 | Kay |
| 2007/0226211 A1 | 9/2007 | Heinze |
| 2008/0040151 A1 | 2/2008 | Moore |
| 2008/0052255 A1 | 2/2008 | Fan |
| 2008/0063279 A1 | 3/2008 | Vincent |
| 2008/0077443 A1 | 3/2008 | Singer |
| 2008/0091633 A1 | 4/2008 | Rappaport |
| 2008/0097936 A1 | 4/2008 | Schmidtler |
| 2008/0103828 A1 | 5/2008 | Squilla |
| 2008/0120296 A1 | 5/2008 | Kariathungal |
| 2008/0147441 A1 | 6/2008 | Kil |
| 2008/0195570 A1 | 8/2008 | Alsafadi |
| 2008/0208630 A1 | 8/2008 | Fors |
| 2008/0250025 A1 | 10/2008 | Abhyanker |
| 2008/0256181 A1 | 10/2008 | Morita |
| 2008/0263048 A1 | 10/2008 | Wise |
| 2008/0270120 A1 | 10/2008 | Pestian |
| 2008/0270340 A1 | 10/2008 | Abrams |
| 2008/0287746 A1 | 11/2008 | Reisman |
| 2008/0288292 A1 | 11/2008 | Bi |
| 2008/0320029 A1 | 12/2008 | Stivoric |
| 2009/0024615 A1 | 1/2009 | Pedro |
| 2009/0048877 A1 | 2/2009 | Binns |
| 2009/0070103 A1 | 3/2009 | Beggelman |
| 2009/0076839 A1 | 3/2009 | Abraham-Fuchs |
| 2009/0099876 A1 | 4/2009 | Whitman |
| 2009/0110287 A1 | 4/2009 | Bates |
| 2009/0112882 A1 | 4/2009 | Maresh |
| 2009/0125246 A1 | 5/2009 | Ruiz Laza |
| 2009/0136102 A1 | 5/2009 | Kimpe |
| 2009/0138287 A1 | 5/2009 | Hermann, Jr. |
| 2009/0198517 A1 | 8/2009 | Ruben |
| 2009/0216696 A1 | 8/2009 | Downs |
| 2009/0220175 A1 | 9/2009 | Tzadok |
| 2009/0228303 A1 | 9/2009 | Faulkner |
| 2009/0228909 A1 | 9/2009 | Huang |
| 2009/0238625 A1 | 9/2009 | Ming |

(56) References Cited

U.S. PATENT DOCUMENTS

| | | |
|---|---|---|
| 2009/0259487 A1 | 10/2009 | Rao |
| 2009/0265189 A1 | 10/2009 | Bartholomew, III |
| 2009/0271221 A1 | 10/2009 | Aridi |
| 2009/0287504 A1 | 11/2009 | Benjamin |
| 2009/0326981 A1 | 12/2009 | Karkanias |
| 2010/0036680 A1 | 2/2010 | Familant |
| 2010/0088107 A1 | 4/2010 | Ur |
| 2010/0117799 A1 | 5/2010 | Dormer |
| 2010/0131299 A1 | 5/2010 | Hasan |
| 2010/0131438 A1 | 5/2010 | Pandya |
| 2010/0131482 A1 | 5/2010 | Linthicum |
| 2010/0145723 A1 | 6/2010 | Hudson |
| 2010/0169123 A1 | 7/2010 | Maus |
| 2010/0174579 A1 | 7/2010 | Hughes |
| 2010/0179827 A1 | 7/2010 | McCallie, Jr. |
| 2010/0185496 A1 | 7/2010 | Hahn |
| 2010/0228721 A1 | 9/2010 | Mok |
| 2010/0274584 A1 | 10/2010 | Kim |
| 2010/0281036 A1 | 11/2010 | Inoue |
| 2010/0310172 A1 | 12/2010 | Natarajan |
| 2010/0324927 A1 | 12/2010 | Tinsley |
| 2010/0324936 A1 | 12/2010 | Vishnubhatla |
| 2011/0004588 A1 | 1/2011 | Leitersdorf |
| 2011/0072002 A1 | 3/2011 | Kirkby |
| 2011/0077972 A1 | 3/2011 | Breitenstein |
| 2011/0078145 A1 | 3/2011 | Chung |
| 2011/0093293 A1 | 4/2011 | G. N. |
| 2011/0093334 A1 | 4/2011 | Wood |
| 2011/0117799 A1 | 5/2011 | Harada |
| 2011/0119089 A1 | 5/2011 | Carlisle |
| 2011/0129153 A1 | 6/2011 | Petrou |
| 2011/0131062 A1 | 6/2011 | Menschik |
| 2011/0196702 A1 | 8/2011 | Salouk |
| 2011/0222768 A1 | 9/2011 | Galic |
| 2011/0225001 A1 | 9/2011 | Shen |
| 2011/0251989 A1 | 10/2011 | Kraaij |
| 2011/0258001 A1 | 10/2011 | Green, III |
| 2011/0264665 A1 | 10/2011 | Mital |
| 2011/0270632 A1 | 11/2011 | Manning |
| 2011/0295775 A1 | 12/2011 | Wang |
| 2012/0041772 A1 | 2/2012 | Ebadollahi |
| 2012/0060216 A1 | 3/2012 | Chaudhri |
| 2012/0066017 A1 | 3/2012 | Siegel |
| 2012/0089412 A1 | 4/2012 | Bardy |
| 2012/0089606 A1 | 4/2012 | Eshwar |
| 2012/0110016 A1 | 5/2012 | Phillips |
| 2012/0166212 A1 | 6/2012 | Campbell |
| 2012/0215578 A1 | 8/2012 | Swierz, III |
| 2012/0239671 A1 | 9/2012 | Chaudhri |
| 2012/0278102 A1 | 11/2012 | Johnson |
| 2012/0284056 A1 | 11/2012 | Hofstetter |
| 2012/0303378 A1 | 11/2012 | Lieberman |
| 2013/0007020 A1 | 1/2013 | Basu |
| 2013/0046529 A1 | 2/2013 | Grain |
| 2013/0124523 A1 | 5/2013 | Rogers |
| 2013/0159023 A1 | 6/2013 | Srinivas |
| 2013/0166317 A1 | 6/2013 | Beardall |
| 2013/0231956 A1 | 9/2013 | Chaudhri |
| 2013/0238349 A1 | 9/2013 | Sethumadhavan |
| 2013/0291060 A1 | 10/2013 | Moore |
| 2013/0297536 A1 | 11/2013 | Almosni |
| 2013/0332194 A1 | 12/2013 | Timothy |
| 2013/0332199 A1 | 12/2013 | Freiwat |
| 2014/0012738 A1 | 1/2014 | Woo |
| 2014/0046697 A1 | 2/2014 | Rogers |
| 2014/0136559 A1 | 5/2014 | Kottaram |
| 2014/0257842 A1 | 9/2014 | Heinze |
| 2014/0278832 A1 | 9/2014 | Glavina |
| 2015/0003667 A1 | 1/2015 | Rowley |
| 2015/0019463 A1 | 1/2015 | Simard |
| 2015/0066537 A1 | 3/2015 | Sheffer |
| 2015/0066539 A1 | 3/2015 | Sheffer |
| 2015/0100572 A1 | 4/2015 | Kalafut |
| 2016/0048643 A1 | 2/2016 | Woods |
| 2016/0292527 A1 | 10/2016 | Kumar |
| 2017/0083785 A1 | 3/2017 | Warsawski |
| 2017/0132314 A1 | 5/2017 | Liu |
| 2018/0011974 A1 | 1/2018 | Schneider |

FOREIGN PATENT DOCUMENTS

| | | |
|---|---|---|
| EP | 0791203 B1 | 4/1998 |
| JP | 09135816 A | 5/1997 |
| JP | 11219403 A | 8/1999 |
| JP | 4471736 B2 | 6/2010 |
| JP | 2010134946 A | 6/2010 |
| KR | 20010002074 A | 1/2001 |
| KR | 100750071 B1 | 8/2007 |
| KR | 1020090050881 B1 | 5/2009 |
| KR | 1020120004749 B1 | 1/2012 |

OTHER PUBLICATIONS

Bentkus et al., "Confidence Bounds for a Parameter" Sep. 2001 Mathematics Subject Classification.

Lemeshow et al., Searching one or two databases was insufficient for meta-analysis of observational studies, 7 pages (Year: 2005).

Natarajan et al., "An Analysis of Clinical Queries in an Electronic Health Record Search Utility" Int. J Med Inforamtics, Jul. 2010.

Rector et al., "Medical-Concept Models and Medical Records: An approach based on GALEN adn PEN PAD" Journal of the American Medical Informatics Association, vol. 2 No. 1 Jan./Feb. 1995.

Rogue et al., "Using Electronic Patient Records to Discover Disease Correlations and Stratify Patient Cohorts" PLoS Computational Biology, Aug. 2011, vol. 7, Issue 8 el 002141.

The Statistics Calculator, StatPac; Dec. 17, 2003, available from: http://web.archive.org/web/20031217141819/http://statpac.com/stati sti cscalculator/percents.htm.

Feature Selection, Apr. 5, 2016, Wikipedia (Year: 2016).

SYSTEMS AND METHODS FOR IMPROVED OPTICAL CHARACTER RECOGNITION OF HEALTH RECORDS

CROSS REFERENCE TO RELATED APPLICATIONS

This application is a continuation of and claims priority to U.S. patent application Ser. No. 15/662,246, filed on Jul. 27, 2017, which is a non-provisional and continuation-in-part application claims the benefit of provisional application No. 62/369,007 filed on Jul. 29, 2016, of the same title, which application is incorporated herein in its entirety by this reference.

U.S. patent application Ser. No. 15/662,246, filed on Jul. 27, 2017, also is a continuation-in-part application and claims the benefit of application Ser. No. 13/223,228, filed on Aug. 31, 2011, entitled "Medical Information Navigation Engine (MINE) System", which issued as U.S. Pat. No. 10,176,541 on Jan. 8, 2019, which application claims priority to U.S. Provisional Application No. 61/379,228 filed on Sep. 1, 2010, of the same title, both applications are incorporated herein in their entirety by this reference.

Additionally, U.S. patent application Ser. No. 15/662,246, filed on Jul. 27, 2017, is a continuation-in-part application that claims the benefit of application Ser. No. 13/747,336 filed on Jan. 22, 2013, entitled "Knowledge Extraction and Exchange Method and Apparatus", which application claims priority to U.S. Provisional Application No. 61/590,330 filed on Jan. 24, 2012, of the same title, both applications are incorporated herein in their entirety by this reference.

BACKGROUND

The present invention relates generally to optical character recognition (OCR) of documents. In particular, the systems and methods disclosed herein relate to enhancements of OCR quality for records that require a high degree of accuracy, such as medical and legal records. Within the context of medical records, the ability to get very accurate OCR of medical documents enables a host of advanced downstream processing, including advanced queries and searches, tagging and automated classification.

Despite rapid growth of innovation in other fields in recent decades, the world of medical information, including patient medical records, billing, referrals, and a host of other information, has enjoyed little to no useful consolidation, reliability, or ease-of-access, leaving medical professionals, hospitals, clinics, and even insurance companies with many issues, such as unreliability of medical information, uncertainty of diagnosis, lack of standard, and a slew of other related problems.

One of the challenges facing those in the medical or related areas is the number of sources of information, the great amount of information from each source, maintenance of data in a HIPAA compliant manner, and consolidation of such information in a manner that renders it meaningful and useful to those in the field in addition to patients. Obviously, this has contributed to increased medical costs and is perhaps largely attributed to the field suffering from an organized solution to better aid the medical professionals, to better aid those requiring more reliable patient history and those requiring more control and access over such information.

The concept of "big data" is already well established in the field of information technology. Big data is a collection of tools, techniques and methodologies used when data sets are large and complex that it becomes difficult or impossible to store, query, analyze or process using current database management and data warehousing tools or traditional data processing applications. The challenges of handling big data include capture, curation, storage, search, sharing, analysis and visualization. The trend to larger data sets is due to the proliferation of data capture devices and the ease of capturing and entering data from a wide variety of sources.

Due to the intrinsic issues prevalent with medical information—where very large amounts of clinical and administrative information are generated and stored as unstructured text and scanned documents, big data platforms and analysis is all but unheard of One major hurdle is that this data cannot be easily and accurately accessed by computer systems. While OCR technology may be applied, often the accuracy of the OCR document is insufficient for advanced downstream analysis. This is especially true across a set of medical records that are from different sources and may result in vastly different levels of OCR quality.

The inability to leverage the entirety of medical data available for a patient and/or cohort of patients results in considerable value being lost by healthcare providers, insurance companies, and patients. For example, a big data platform could enable solutions utilizing all of the data to optimize accurate risk assessment, population health, and revenue for value-based healthcare organizations. Without such a platform, these value added solutions are less obtainable.

It is therefore apparent that an urgent need exists for tools that allow for the analysis of medical information in order to make downstream processing of the data possible. Specifically, the ability to improve OCR quality over what is currently available would significantly improve downstream analytics of the data

SUMMARY

To achieve the foregoing and in accordance with the present invention, systems and methods for improved optical character recognition (OCR) of health records is provided. Such systems and methods enable the rapid and accurate translation of free-form records into data that may be processed by downstream analytics.

In some embodiments, an image of a medical record may be received, and an initial optical image recognition (OCR) on the image may be performed to identify text information. Any known OCR technique may be implemented for this OCR process. The OCR signal quality may be measured, and areas of insufficient OCR signal quality may be isolated. The OCR process may be repeated on the isolated regions of lower signal quality, each time using a different OCR transform, until all regions are completed with a desired degree of signal quality (accuracy). All the regions of the document may then be recompiled into a single document for outputting.

In some embodiments, the signal quality is determined by a weighted average of semantic analysis of the resulting text, and/or OCR accuracy measures. In some cases, the signal quality is determined by maximizing entropy within the OCR area being analyzed in a linear model. The regions are isolated for further analysis, or segmented initially in some embodiments, by identifying regions of contiguous signal quality within the OCR image.

Note that the various features of the present invention described above may be practiced alone or in combination. These and other features of the present invention will be described in more detail below in the detailed description of the invention and in conjunction with the following figures

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1:
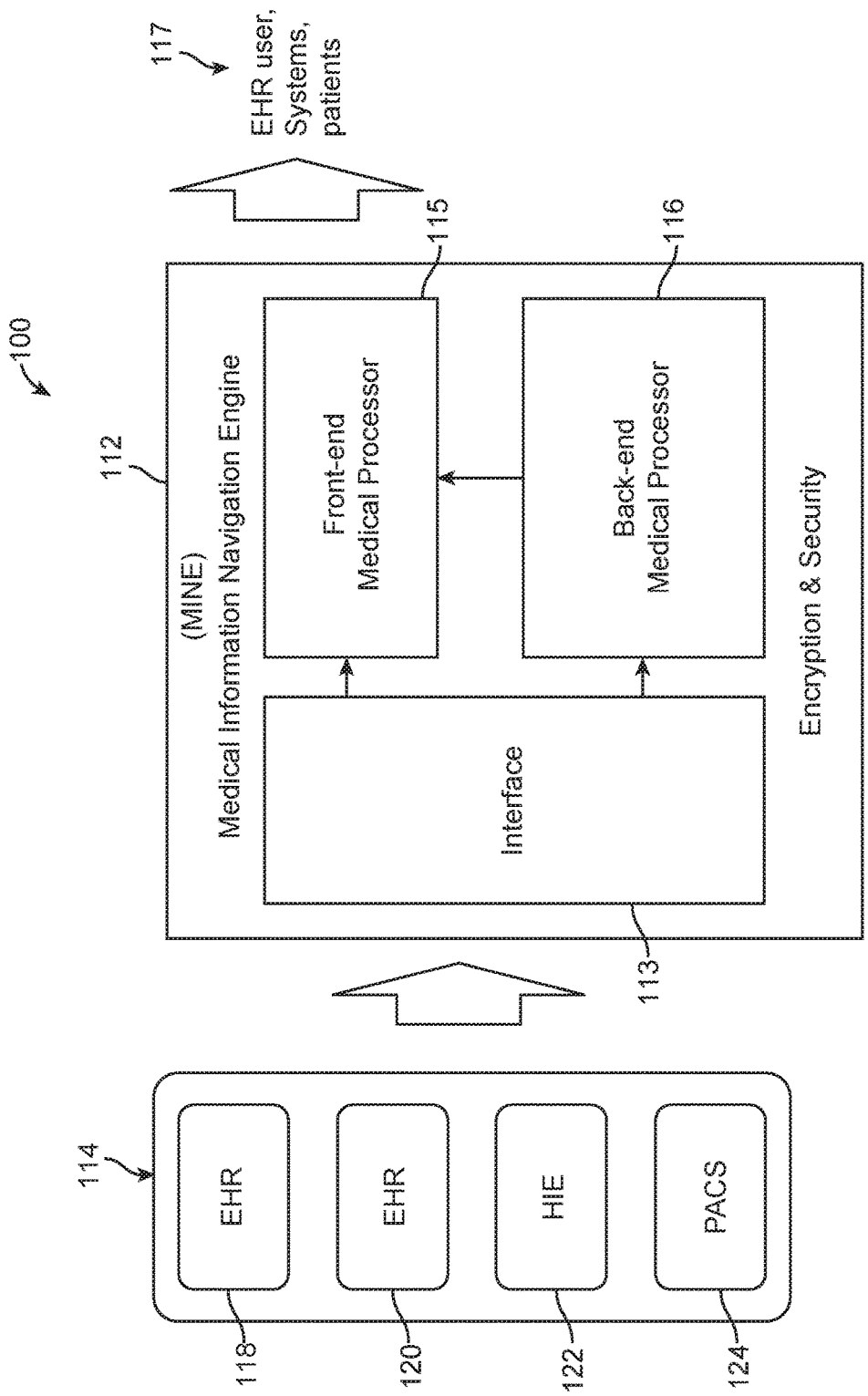
FIG. 1 shows a medical information system, in accordance with some embodiments.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

The present invention relates to the optical character recognition (OCR) systems and methods. More particularly, the present disclosure focuses on the advancement of OCR techniques in order to more accurately interpret a free form record. This advanced OCR technology will be referred to as "autofocus OCR" throughout this disclosure for the sake of brevity.

Within the field of medical record big-data, such accuracy of records is required to perform much of the downstream analysis that provides value to insurers, medical care professionals and the patients. While this disclosure will focus almost exclusively upon the autofocused OCR, it should be understood that these systems and methods may be applied to any situation where extensive free-form records require OCR analysis with a high degree of accuracy. Thus while the medical field is provided by way of example, it should be readily understood that these techniques may be applied to the legal field, business operations, research, archiving, or virtually any applicable field.

For example, in some embodiments the disclosed system is a flexible, highly-scalable big-data enterprise system that understands concepts, and associations and relationships between the concepts from unstructured text using machine learning and NLP (natural language processing) techniques. The system is completely language independent and domain independent as it extracts the concepts and relationships directly from its input text. Thus, the autofocus OCR features can be constructed and utilized across multilingual documents (and thus also serve as a translational tool) and can also be utilized across multiple domains (e.g.: Healthcare, Legal, etc.). In fact, even within the field of healthcare, the data does not all need to be medical in nature. The data can be of variety of types including administrative, workflow, process, inventory, lifestyle, technology, etc. As such, it is considered that any situation where big data analysis is desirable may be within the scope of this disclosure. Again, note that the discussion contained herein will primarily be centered on medical information for the sake of clarity and specialized examples.

The following description of some embodiments will be provided in relation to numerous subsections. The use of subsections, with headings, is intended to provide greater clarity and structure to the present invention. In no way are the subsections intended to limit or constrain the disclosure contained therein. Thus, disclosures in any one section are intended to apply to all other sections, as is applicable.

I. Medical Systems

To facilitate the discussion, FIG. 1 illustrates a medical system 100, in accordance with an embodiment of the invention. The system 100 is shown to include medical source 114, a medical information navigation engine (MINE) 112, and medical information consumers (also referred to herein as "output" or "medical output") 117. The medical source 114 are shown to include an electronic health record (EHR) 118, EHR 120, health information exchange (HIE) 122, and a picture archiving and communication system (PACS) 124. The MINE 112 is shown to include interface 113, a back-end medical processor 116, and a front-end medical processor 115.

The MINE 112 disclosed herein, is capable of receiving medical information data, and de-duplicating, converting the information into machine readable data, indexing and tagging the data in order to allow for downstream analysis. "Medical information", as used herein, refers to any health-related information, including but not limited to patient medical records, patient entered information, care team entered information, healthcare device generated information, and billing information.

The source 114 generally provides various medical information to the MINE 112. For example, the EHRs 118 and 120 each may provide information such as medical records and billing, the HIE 122 may provide information such as medical records, and the PACS 124 may provide information such as diagnostic imaging and reports.

The medical information consumers 117, which may be made of a host of entities or individuals, such as patients, clinics, medical institutions, health organization, and any other medical-related party, use information that is provided by the processor 115 of MINE 112 and that can, by way of example, consist of patients, medical systems, medical organization administrators, medical researchers, and/or EHR users. For example, user-customized processed medical information (indexed and tagged) is provided by the processor 115 to a number of users within the medical information consumers 117. In this case, the processor 115 generates user-customized processed medical information to a plurality of users, with at least a portion of the user-customize processed medical information being provided to each of the users based on the relevancy of the portion being provided of each user's specific function or role and each user's associated security privileges.

The processor 116, in some embodiments, indexes identifies, maps, and consolidates medical information, received from the interface 113, and tags this information, and determines to reconcile the tagged information. In some methods and embodiments, information that is extracted from images via optical character recognition (OCR), as will be discussed in considerable detail below. The extracted data is then tagged to enhance recall of search queries. Indexing, at least in part, processes document and converts them into formats that allows for quick searching across a large collection of documents. The records, once processed, are then subject to automated classification and additional downstream analytics.

The information in the MINE 112 is encrypted and secure to ensure privacy of sensitive medical information. Likewise, any final event streams provided to downstream applications may be encrypted or otherwise anonomized in order to comport to HIPAA and other privacy regulations.

It is understood that the sources 114 of FIG. 1 includes merely some examples of the sources that communicate with the MINE 112 and that other sources, known to those in the field, are contemplated. Similarly, the output 117 may be used by those or entities not discussed herein but that are contemplated and within the scope and spirit of the invention.

The interface 113 serves to receive information that is in various forms, such as but not limited to text, html, CCD, CCR, HL7 and any other type or formatted information. The interface 113 then provides to the processors 115 and 116 information, as needed.

The processor 116 receives some of the medical information that the interface 113 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 116 recognizes that the records belong to a single individual or are the same data and just recorded differently and automatically consolidates them. The patient or a user of the system 100 may also manually perform reconciliation. The processor 116 advantageously determines whether or not reconciliation is performed.

The processor 116 outputs the indexed, tagged and reconciled information to the processor 115. The foregoing tasks are a generalization, and further details of each are provided below.

The processor 115 performs certain tasks on the information provided by the interface 113 and the processor 116, which include query, search, presentation, and quality checking, and ultimately downstream analysis, such as classification, coder sorting, or the like. The output of the processor 115 may be an indexed document, or output 117.

The MINE 112, through the processor 115, in some embodiments and methods, invites members of a medical care team to join it thereby allowing distributed user-organized care teams.

Querying, as performed by the processor 115, is the ability to receive, as input, a free text query, from a user, (e.g., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries.

Search, as performed by the processor 115, is built around the concept of Zero-Click Relevance—or the ability to get to all the relevant information an actor in the healthcare system requires by typing in just a single query. The search engine, within the processor 115, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 117 and security privileges are either determined by the MINE 112 or by the patient or both. The information that is uploaded to the MINE 112 by users, such as in output 114 (in some embodiments) is searched by the processor 115. The uploaded information may include information such as but not limited to status posts, records, and images. Such user-uploaded information is routed automatically to the output 117, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 112. He is presented with relevant lab results, such as CKMB, troponin, and amylase, relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term.

In Joan's case, a search for "chest pain" returns a CKMB lab result and a reference to the most recent chest CT scan. Accordingly and advantageously, the Lexical and Medical concept search solves Dr. Smith's information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 115, is displaying health information to the requesting user in a way that reduces the number of clicks and maximizes the amount of meaningful information delivered based on the interpreting the intent of the user query.

Quality checking, as performed by the processor 115, is checking of the quality of medical information provided by various sources, i.e. source 114, by the patients, structured data, and unstructured data, in a Wiki-like mannered setting whereby the users can help maintain and improve the quality of information displayed. The foregoing tasks, performed by the processor 115, are further described in detail below. Additionally, the users or patients may make comments regarding medical information, in a Wiki-like manner.

In summary, the MINE 112 transacts medical information including the interface 113 receiving medical information from a number of medical sources (such as within the source 114) for processing, identifying, mapping, consolidating, and classifying by the medical processor 116, providing access to specific relevant data, based on a user's security privileges, within the identified, mapped, and consolidated medical information, based on user-specific functions or roles, performed by the processor 115, and generating user-customized processed medical information to a number of users, such as within the output 117, with at least a portion of the user-customized processed medical information being provided to each of the users based on its relevancy to each user's specific function or role and each user's associated security privileges.

Figure 2:
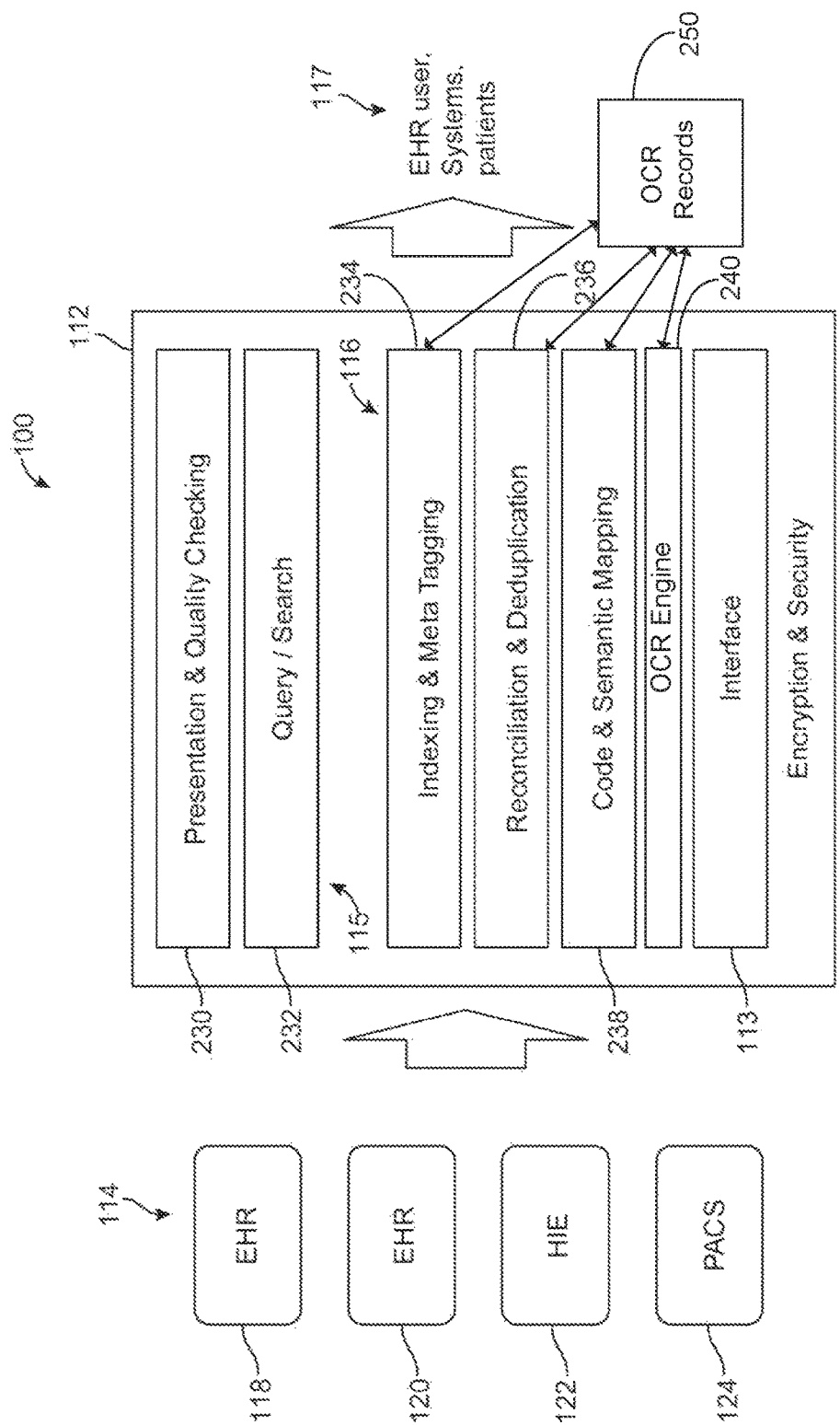
FIG. 2 shows further details of the system, particularly the Medical Information Navigation Engine (MINE) thereof, in accordance with some embodiments.

FIG. 2 shows further details of the system 100, particularly the MINE 112 thereof. That is, the processor 116 is shown to include an indexing and meta tagging module 234, which includes an indexing module and a meta tagging module (both of which are not shown in FIG. 2 in the interest of clarity), which may be a module, as shown in FIG. 2 or two physically separate modules. The processor 116 is further shown to include a reconciliation and de-duplication module 236, which also can be broken out into two modules, a reconciliation module and a de-duplication module, and a code and semantic mapping module 238, which also may be a single module or multiple modules. The output of the tagging module, reconciliation and semantic mapping is processed data for consumption by the HER user or other downstream systems 117.

Prior to indexing and reconciling the data, an OCR engine 240 may consume free-form electronic medical records and convert them into machine readable data sources. As is well known, a number of systems and methods exist for the optical character recognition of data. Traditional optical character recognition relies upon having access to a large repository of text font styles and canonical character representations. The processing involves template matching for the input character images.

These "font matching" OCR systems have the drawback of being font dependent, and suffer in accuracy when a given document includes novel font styles. Alternate OCR methods group together similar characters within the document and solves cryptograms to assign labels to clusters of characters. Patterns can be identified in such systems (such as document image distortion) in order to enhance OCR accuracy even in individualized documents. Additionally, more recent advancements have been made in using statistical machine translation (SMT) techniques to convert image information into machine readable data.

The OCR engine 240 displayed here may have access to any one of the known OCR techniques discussed above, as well as any OCR techniques known in the art that may be useful for converting the image data into textual data. However, the instant autofocusing OCR engine goes beyond merely employing known OCR techniques, and parses the images by similarity, and performs separate OCR functions on each segment. The accuracy of each segment's OCR is computed, and compared to a threshold value. Sections that are deemed as being insufficient are then iteratively reprocessed by alternate OCR techniques until all sections are deemed sufficient, or until all techniques are exhausted. In the case where no OCR methodology is capable of generating a sufficient result, the technique with the 'best' output may be utilized, and the section may be flagged for user intervention and review. The output of the OCR engine 240 are the OCR records 250, which are consumable by the modules 234, 236 and 238.

The foregoing modules may be software programs, executed by a computer or computing engine of suitable sorts, or may be implemented in hardware.

Figure 3:
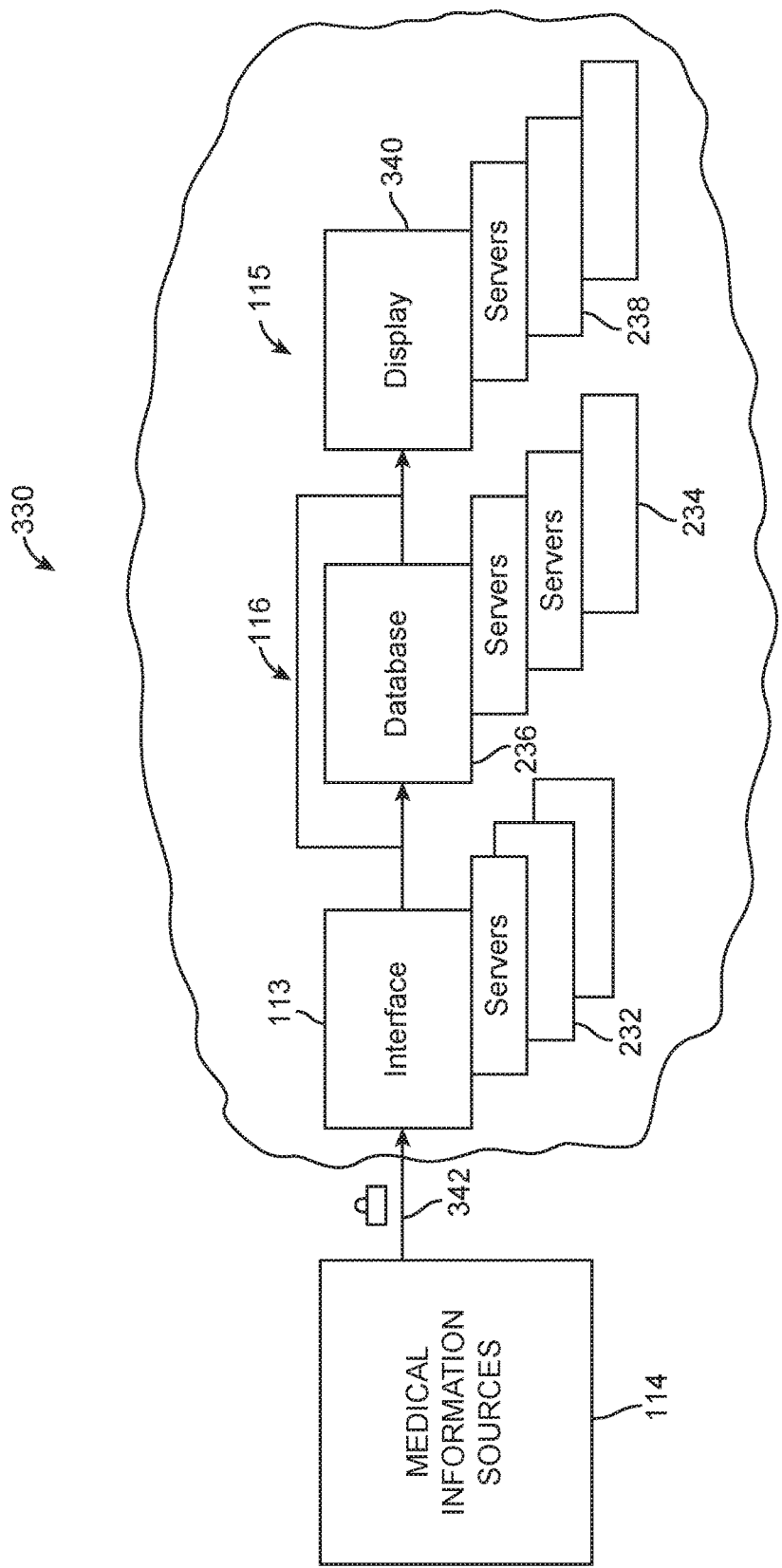
FIG. 3 shows an exemplary embodiment implementing the system using various devices, in accordance with some embodiments.

FIG. 3 shows an exemplary embodiment implementing the system 100 using various devices. That is, the medical system 330 is analogous to the system 100 and is shown to include the sources 114 coupled to communicate, securely, through the secure communication link 342, to the interface 113. The link 342 may be any suitable communication channel allowing information, of various formats and types, to be transferred to the interface 113 in a secure and encrypted fashion. Exemplary communication channels of which the link 342 is made include the Internet, VPN connections over the Internet, private dedicated digital lines such as T1, T3, E1, E3, SONET, and other fiber optic formats.

The interface 113, in some embodiments, is a software program that executes on one or more servers 232, which can be a server of any kind of suitable computing engine, such as personal computer (PC). The servers 232 receive secure information through the link 342 from the sources 114. The processor 116, in some embodiments, includes the module 236 and one or more servers 234, which may be any suitable computing engine, similar to the servers 232, including but not limited to PCs or servers.

The module 236 and servers 234 perform the tasks discussed above relative to the processor 116 and the display 340 and servers 238 perform the tasks discussed above relative to the processor 115 though these processors may and often perform additional tasks related to medical information, some examples of which are presented and discussed below and the rest of which are contemplated and achieve the various advantages, results and functions presented herein.

The processor 115, in some embodiments, includes display and visualization 340 executing on one or more servers 238, which may be any suitable computing engine, similar to the servers 232, including but not limited to PCs or servers. The display 340 is used to construct presentation and display information to users, such as the patient's records, billing information, and other types of medical information. The display 340, in some embodiments, also performs processing of some of the functions of the processor 115.

As shown in FIG. 3, the servers 232 are coupled to the module 236 and the servers 234, and to the display 340 and the servers 238 and the module 236 and servers 232 are coupled to the display 340 and the servers 238.

In some embodiments, the interface 113, servers 232, module 236, servers 234, display 340, and servers 238 are remotely located relative to the sources 114 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4:
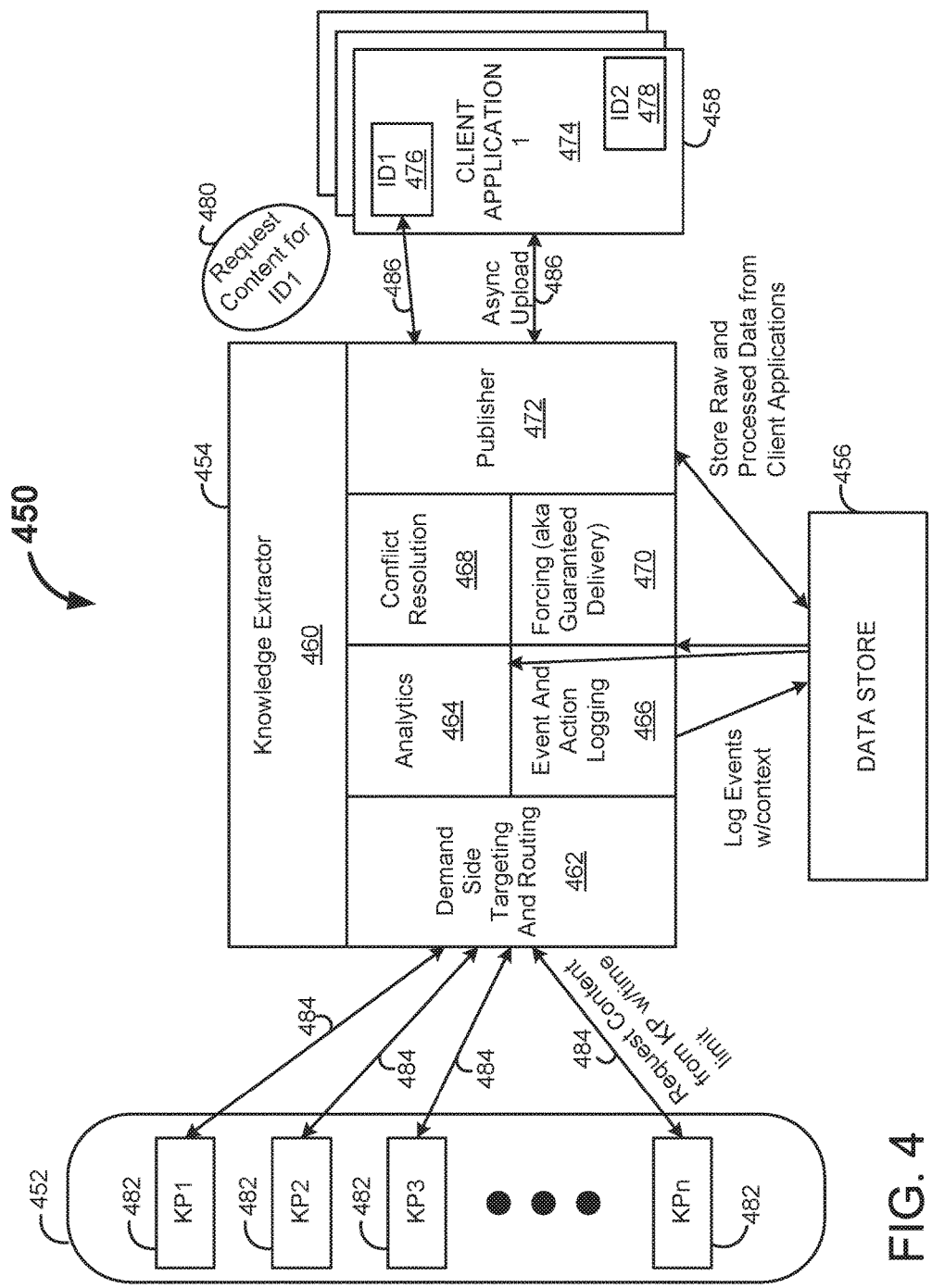
FIG. 4 shows a block diagram of a knowledge extraction system, in accordance with some embodiments.

FIG. 4 shows a block diagram of a knowledge extraction system 450, in accordance with an embodiment of the invention. The knowledge extraction system may be functionally separate from the MINE 112, or may be an integrated feature of the MINE 112, hosted by one or more of the processors 116. Critical to knowledge extraction is the ability to accurately perform text recognition in images of the medical records.

The system 450 is shown to include a knowledge provider block 452, a knowledge extraction and exchange unit 454, a data store block 456, and a client application block 458. The block 458 executes client or user applications 474 using output generated by the knowledge extractor 460.

The block 452 is analogous to the sources 114 of FIG. 1 and is shown to include a number of knowledge providers 482, with each knowledge provider being analogous to one of the sources discussed above relative to the sources 114. The knowledge extraction and exchange unit 454 may include the back-end medical processor, shown in FIGS. 1 and 2. The knowledge extraction and exchange unit 454 is shown to include a demand-side targeting and routing block 462, an analytics block 464, an event and action logging block 466, a conflict resolution block 468, a forcing (or guaranteed delivery) block 470, a publisher block 472, and a knowledge extraction block 460. The block 458 is shown to include one or more impression domain (ID) blocks 476 and 478. While two ID blocks are shown in FIG. 4, it is understood that any number of ID blocks (e.g. problems, procedures, medications, allergies, "did you know?", patient safety items, billing enhancement items, and the like), as required by a user of the system 450, may be employed.

The knowledge extraction and exchange block 454 generally manages the overall process of delivering "content" to the ID blocks 476 and 478, including managing the data store block 456, managing interactions with the knowledge providers 482 and determining which results to present to the client application block 458 (which is generally analogous to the front end processor 115 of FIGS. 1 and 2) when a request of "content" is made by one of the ID blocks 476 and 478 and how to rank the requested results. An example of a request is shown at 480 in FIG. 4 where the block 476 is making the request. "Content", as used herein, refers to any information pertinent to the ID, for example a query string, image or hyperlink.

The data store block 456 is generally a storage device or a database storing raw and processed data received from the block 474, through the unit 454. Raw data is data that comes directly from the application 474. Processed data is data that has been processed or optimized for efficient use by knowledge providers. The knowledge extraction and exchange block 454 causes actions to be logged with context into the data store block 456 when data is being stored therein.

The knowledge extraction and exchange block 454 communicates with the client application block 458 bi-directionally and typically asynchronously such that when there is a change to the underlying data in the application of the block 458, such as an update to the patient chart, the block 458 sends this updated data to the publisher block 472. The client application block 458 is a client or user application with each of its ID blocks querying for and displaying its particular impression domain content. By way of example only, impression domain content includes items such as problems, procedures, medications, allergies, "did you know?", patient safety items, billing enhancement items, and so on. Each ID presents information to the user that is relevant to the specific patient/user/context at the time the information is displayed. For example, a patient safety ID would present a patient's past history of myocardial infarction to a primary care provider if that event were not noted as structured data the user's EHR application. The publisher block 472 receives content requests from the ID blocks 476 and 478 and in response returns content to be displayed in the blocks 476 and 478. Further, the block 472 receives actions (such as clicks) from the ID blocks 476 and 478, receives raw data (such as patient chart updates) from the application block 474, and manages storage of data in the data store block 456 (including action logs, raw client application data, and data extracted for the specific needs of the knowledge providers 482 of the block 452).

The demand side targeting and routing block 462 routes content requests to the different knowledge providers 482, received from the client application block 458 by selecting a subset of knowledge providers in real time which it considers most relevant to the current patient/user/context based on criteria provided by the knowledge provider, such as "patient covered by Medicare Advantage", "user is a cardiologist", or "query includes the term EKG", and subsequently receives their responses, through the knowledge provider links 484. In some embodiments, if a knowledge provider 482 with an outstanding content request does not respond within a prescribed amount of time, the request is canceled.

The conflict resolution block 468 receives content from the demand side targeting and routing block 462 and advantageously determines which of the responses from the knowledge providers 482 to pass to the forcing block 470 and in which rank order. The conflict resolution block 468 uses the content from the ID block 476 or 478 (e.g., patient, user, query) along with analytics on the performance of past knowledge provider results to determine which results are most likely to be useful. For example, if an endocrinologist user always clicks on the hemoglobin a1c history after performing a diabetes search, the ID for labs may start automatically displaying the history in response to a diabetes context for that particular user. If enough endocrinologists perform the same action, the ID for labs may start automatically displaying the history for all endocrinologists, whereas such an automatic action might not be performed for general practice users searching for the same diabetic context.

The forcing block 470 receives ranked and selected results from the conflict resolution block 468 and further determines to potentially override the ranking determined by the conflict resolution block 468. For example, if only one result can be displayed in a particular ID block, and it receives a high-value reimbursement result and an important patient safety result, the patient safety result might be given priority over the reimbursement result.

The event and action logging block 466 stores action data, such as click-through actions in the data store block 456, along with context information (ID context, date, time). Action data refers to end user actions, e.g., clicking on a particular content that is displayed for more information or history.

The analytics block 464 computes summary statistics for events and actions and places them in the data store block 456 for use by the conflict block 468. End user statistics like click-through rates and dwell times may also be computed by the analytics block 464.

Each of the ID blocks 476 and 478 sends a request to the knowledge extraction and exchange unit 454 asking for certain kinds of result (text, images, links, diagnosis codes) from the knowledge extraction and exchange unit 454. A typical request includes the number of results desired and the context of the request, such as patient identifier, user identifier (and user role, such as specialty, physician or coder or medical assistant, etc.) and the search query. The ID block 476 or 478 is responsible for determining how the results are presented to the user of the system 450. For example, when an action is taken, such as a click on a search link, the ID block 476 or 478 also submits this information to the action logging block 466.

Each of the knowledge providers 482 computes and returns results that are relevant to a particular ID block request. In some embodiments, the knowledge providers 482 have access to the data store block 456. For example, a knowledge provider might return PubMed articles, up-to-date articles, or best treatment practices that are relevant to the patient/user/context.

II. Autofocused Optical Character Recognition

Now that the broad concept of medical information processing and management has been discussed in considerable detail, attention shall now be focused upon the autofocused OCR of medical record images. As noted above, the ability to accurately transform image data into machine readable text is central to the indexing, query and any downstream applications, such as knowledge extraction and classification.

Figure 5:
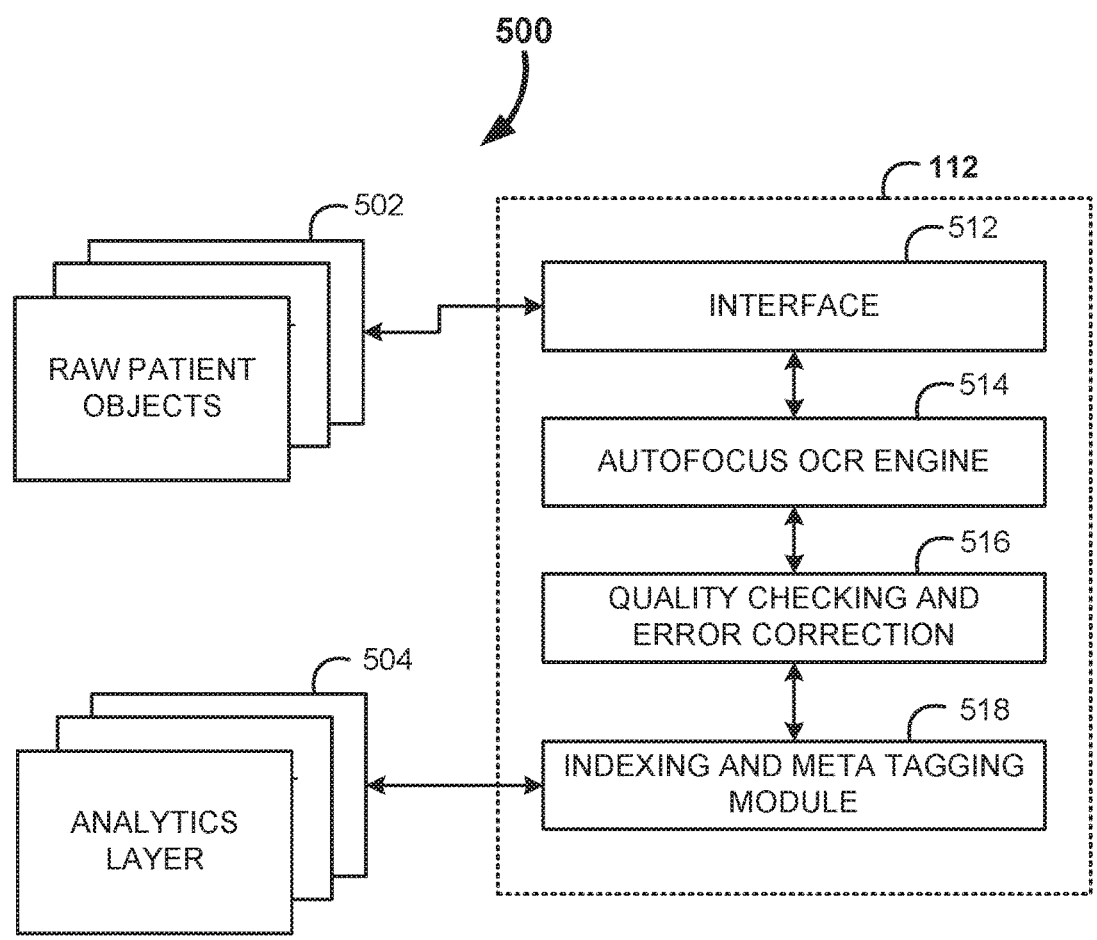
FIG. 5 shows a flow chart of some of the steps performed by the knowledge extractor including the autofocused OCR, in accordance with some embodiments.

Referring to FIG. 5, a block diagram for one embodiment of the system 500 is illustrated, where the raw data objects 502 are received, processed, and analyzed. The raw data objects 502 may include electronic health records of the many varieties already disclosed. This data is received by an interface 512 of the medical information system 112. As discussed previously, this interface may include any known mechanism for secure data transmission from the data source into the MINE 112.

The records are then subject to optical character recognition (OCR) in order to generate a machine readable dataset in the autofocus OCR engine 514. As previously discussed the OCR engine 514 may utilize any known OCR methodologies in order to accurately transform the image data into textual data. However, unlike any current OCR mechanism, this OCR engine 514 parses the document to identify contiguous regions of similarity. The system then iteratively processes each of these sections independently with different OCR transforms in order to identify suitable OCR techniques for each section. The results are subsequently recompiled into a whole document for output. Specifics of the process utilized by the OCR engine 514 will be discussed in considerable detail further below.

The machine readable records are then processed by a quality checking and error correction module 516 for de-duplication of records, and other error correction measures. The cleansed data is then processed by an indexing and meta-tagging module 518 to generate indexed and meta-tagged data. Indexing may include parsing the records and identifying concepts using natural language processing (NLP) techniques. The resulting data may be stored within an analytics layer 504 for downstream processes. As already touched upon, these downstream processes may include annotation, search and query, and additional analytics including automated classifier generation.

Figure 6:
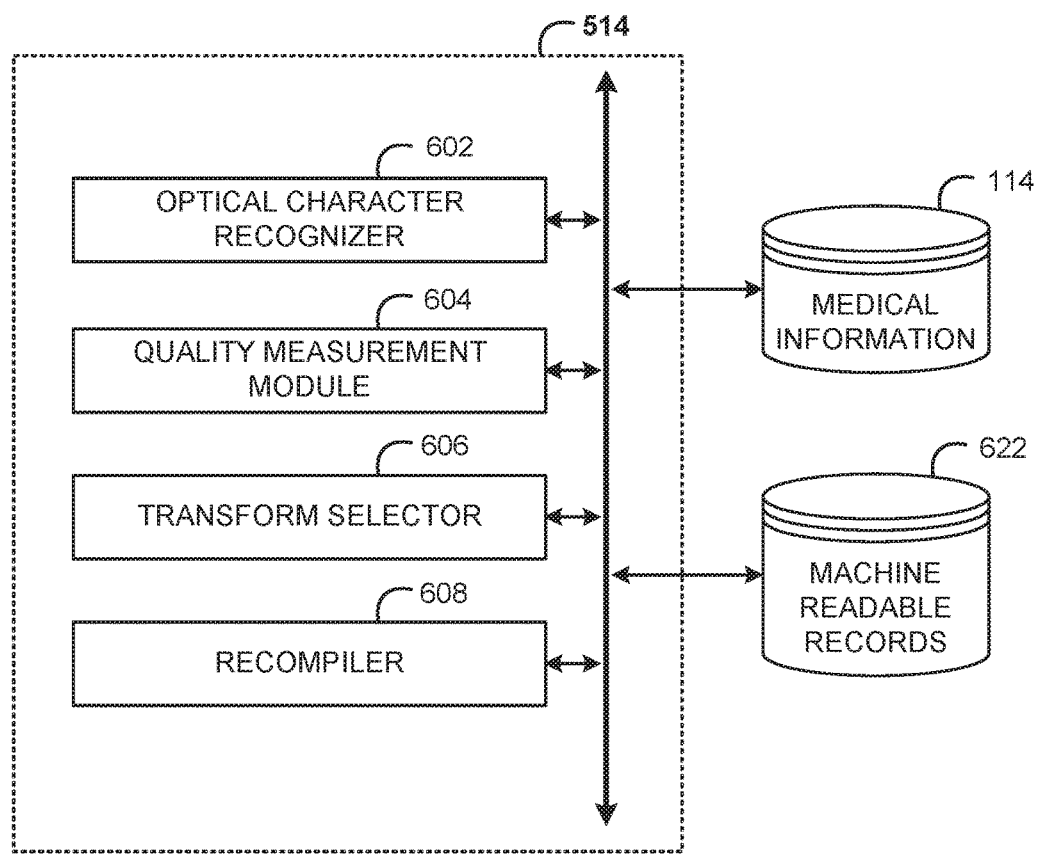
FIG. 6 shows an example of the autofocused OCR engine, in accordance with some embodiments.

FIG. 6 shows a more detailed example of the autofocus OCR engine 514, in accordance with some embodiments. In this example, the medical information 114 in free-format, including as images, is consumed in order to generate an output of machine readable records 622. Initially the medical documents are segmented by a segmentation module (not illustrated). This segmentation breaks apart the document into contiguous portions that exhibit similarity. After segmentation, each segment may be subjected to character recognition.

At its core, the OCR engine 514 includes an OCR module 602 which is capable of performing known OCR analysis. A quality measurement module 604 looks at the level of accuracy of the OCR to determine if the analysis meets the desired quality standards, or if it is of insufficient quality. Depending upon OCR technique employed, different algorithms may be utilized to determine a statistical measure of OCR accuracy. For example, when performing a font comparison OCR method, the system may calculate a figure of merit equation between the document characters and the example font. The degree between which the image varies from the best matched font may indicate the relative error of the OCR.

A transform selector 606 chooses a different transform for the OCR module 602 to apply to any segment which has been determined to be of sub-standard quality. This process may be iterative, where each segment is subjected to different OCR transforms, and the quality is subsequently measured. This iterative process may be repeated until all document segments have undergone an OCR that meet the desired accuracy levels. If all transforms are exhausted for a segment, and none meet the desired quality rating, the transform with the highest accuracy may be utilized, and the segment may be annotated in order to ensure it receives additional attention by a user.

Once all segments have been independently subjected to various OCR events, the final step is to recombine the segments into a complete document. The recompiler 608 performs this action in order to generate the machine readable records 622.

Figure 7:
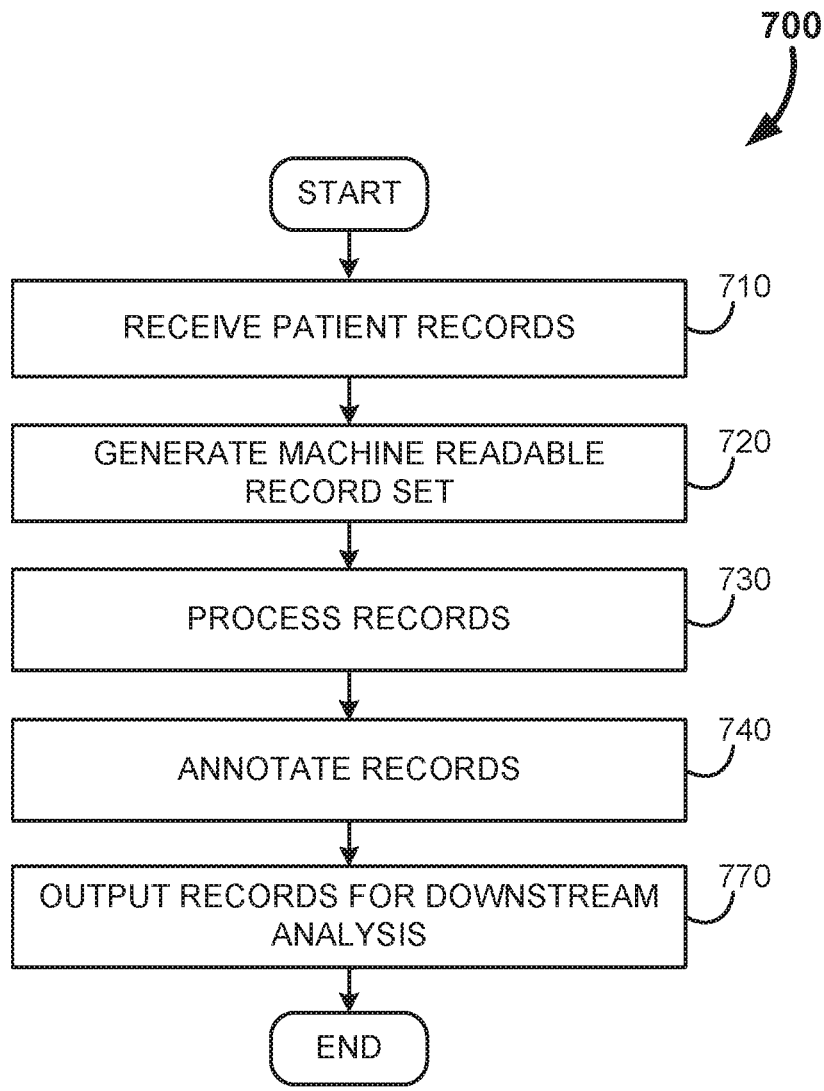
FIG. 7 shows a flow chart of an example method for analyzing medical documents, in accordance with some embodiments.

Continuing on, FIG. 7 shows a flow chart of an example method 700 for analyzing medical documents with this autofocus OCR, in accordance with some embodiment. In this example process, the patient records are initially received (at 710). The medical records, as previously discussed may take the form of patient charts, records, laboratory results, handwritten notes, radiological images, and the like. These records are subjected to the autofocus OCR process in order to generate machine readable documents (at 720).

Figure 8:
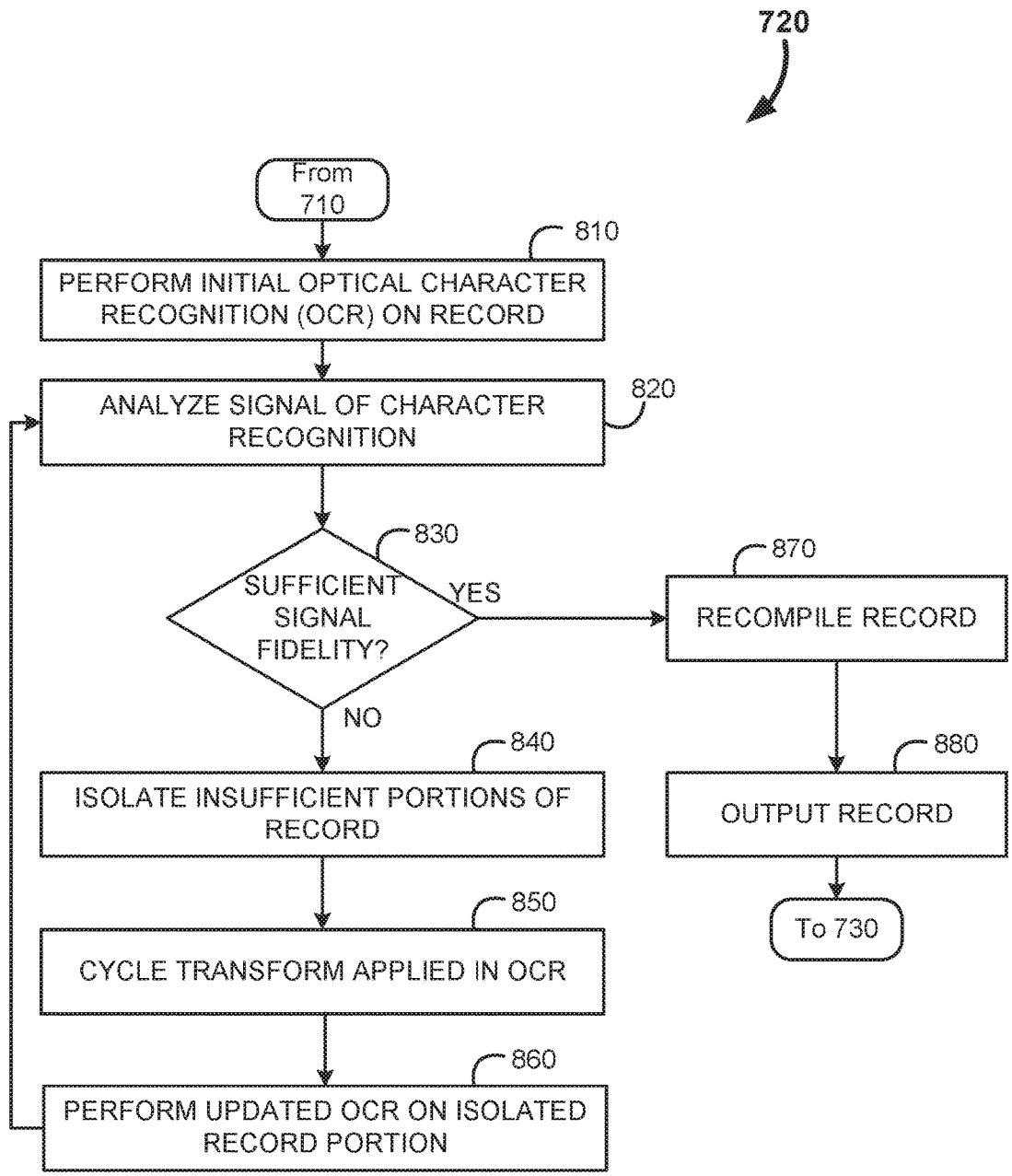
FIG. 8 shows a flow chart of an example method for the autofocused optical character recognition of the medical records, in accordance with some embodiments.

FIG. 8 provides a more detailed flowchart for an example process for the autofocus OCR process. In this example process, the document is initially subjected to optical character recognition (at 810). As previously discussed, many OCR methodologies are known; and any technique, or combination of techniques, may be employed in order to generate records with a high degree of confidence that the information has been properly identified. After OCR completion the signal of the character recognition is analyzed in order to measure OCR accuracy (at 820).

A determination is made whether signal has sufficient fidelity (at 830). The signal quality may be determined by a weighted average of semantic analysis of the resulting text, and/or OCR accuracy measures. In some cases, the signal quality is determined by maximizing entropy within the OCR area being analyzed in a linear model. If the signal is sufficient (above a threshold accuracy level), then the record may be recompiled (at 870) if segmented previously, and the machine readable record may be output (at 880). However, in the circumstance that the signal is not sufficient, the areas of the document that have an insufficient OCR signal level are isolated (at 840). Sections may be isolated by finding contiguous regions of similar signal quality.

The OCR transform may be cycled (at 850), and an update of the OCR analysis may be performed on the isolated sections (at 860). The signal level for these newly analyzed portions may be reassessed (at 820), and the process may repeat as many times as needed with different OCR transforms until all sections of the record are found to have sufficient signal levels.

In an alternate process (not illustrated), rather than performing the character recognition on the entire document and isolating out sections that are insufficient, the alternate process may initially segment the record into portions that have similar attributes. Each of these segmented sections may then undergo a similar process as those shown in FIG. 8, whereby different transforms are applied until each of the segmented sections are found to have sufficient signal. The segments are then recompiled in much the same manner before being output. By segmenting initially, the process may be made more efficient for complicated documents, or documents that have low image quality. Alternately, the illustrated method may be advantageous when the documents are relatively short, consistent or of higher image quality (by avoiding the initial segmentation step). In some other embodiments, the document may be initially processed to determine which enhanced OCR system would be best to apply (e.g., long and low quality documents would be subject to segmentation, whereas shorter and higher quality documents would undergo OCR upon the entire document before isolation of regions with lower signal).

Figure 9:
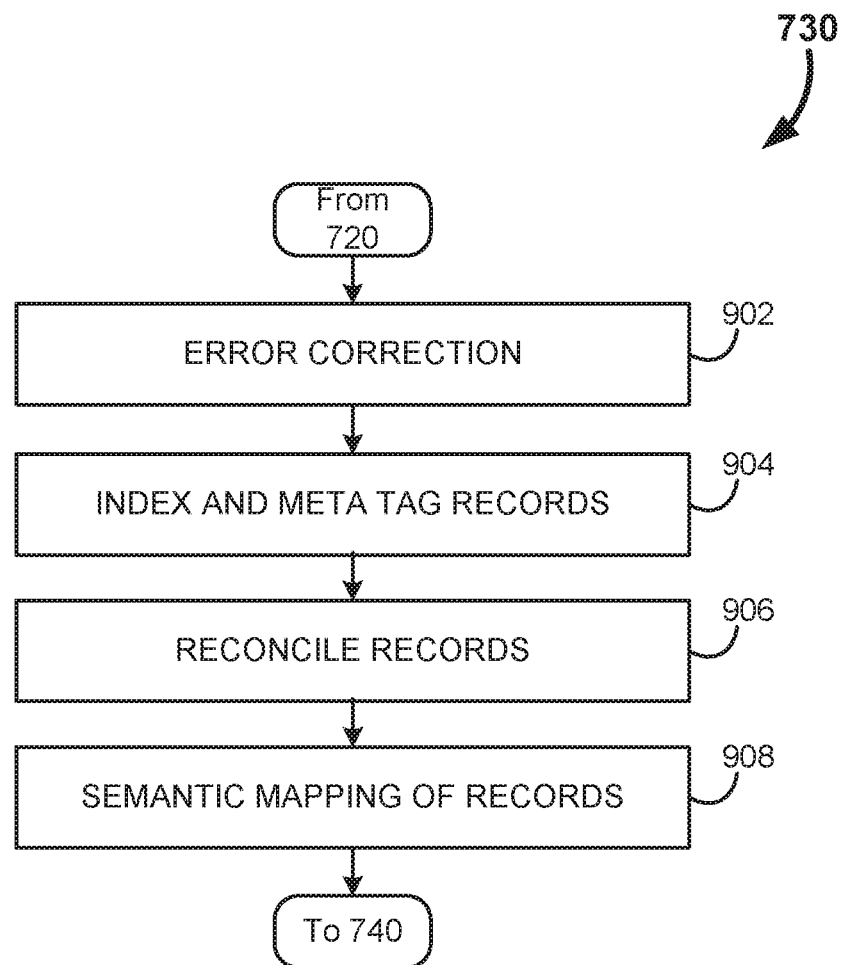
FIG. 9 shows a flow chart of an example method for processing medical documents, in accordance with some embodiments.

Returning to FIG. 7, after the machine readable records have been generated, the records are processed (at 730) in order to make them more suited for further downstream analytics. FIG. 9 shows one example method for this processing of the medical documents, in accordance with some embodiments. Initially the record processing involves error correction (at 902). Error correction includes de-duplication of records, removal of records that are believed to not belong within the dataset (for example records that are for someone of the same name, but is otherwise distinguishable from the actual patient), and obviously erroneous records (such as negative numbers or numbers that are outside of the realm of possible).

After error correction, the records may be indexed and meta-tagged (at 904). Indexing takes processed documents and converts them into formats that make it easy to quickly search across a large collection of documents. Semantic meta-tagging embeds information into the medical information that is relevant thereto and that can be later used to search for certain information for the purpose of reconciliation (at 906) and search, among many others. Next, the records undergo semantic mapping (at 908). Semantic mapping may employ known natural language processing techniques, rules based systems, predictive modeling, or any combination thereof. In some embodiments, rule based systems can learn through history, ontology, user-input, the type of user, and a host of other factors, similarities between various information. The system then models the data conceptually by mapping data based on rules for disease/diagnosis relationships, medications, etc. Timing rules may likewise be applied to see how data has changed over time.

Returning to FIG. 7, after the records have been processed, it may be possible for a physician, administrator, agent or other suitable individual to annotate the records (at 740). Record annotation includes the ability to highlight information of particular interest in the records, and/or associate notes with particular regions of the medical records. Not all documents are necessarily annotated. In some embodiments the annotation step may even be omitted.

After annotation the resulting records may be output (at 770) for additional downstream analysis and consumption by subsequent applications. For example, records may be utilized by a coding verification system, classification system, or even directly to a billing application. The indexed records may be made available in a research exchange, or stored for future analytics.

Applications may provide value to the healthcare organization and patients. For example, a quality optimization application may generate actionable care notifications based upon the analyzed records and classifications. Population analyzers may be a flexible search and query tool that enables the generation of dashboards for risk assessment, performance, compliance, utilization disease registry, and referral management. A HCC optimizer may improve condition capture and risk assessment. It may also monitor coder quality and effort to improve revenue forecasting and reimbursements.

III. System Embodiments

Figure 10A:
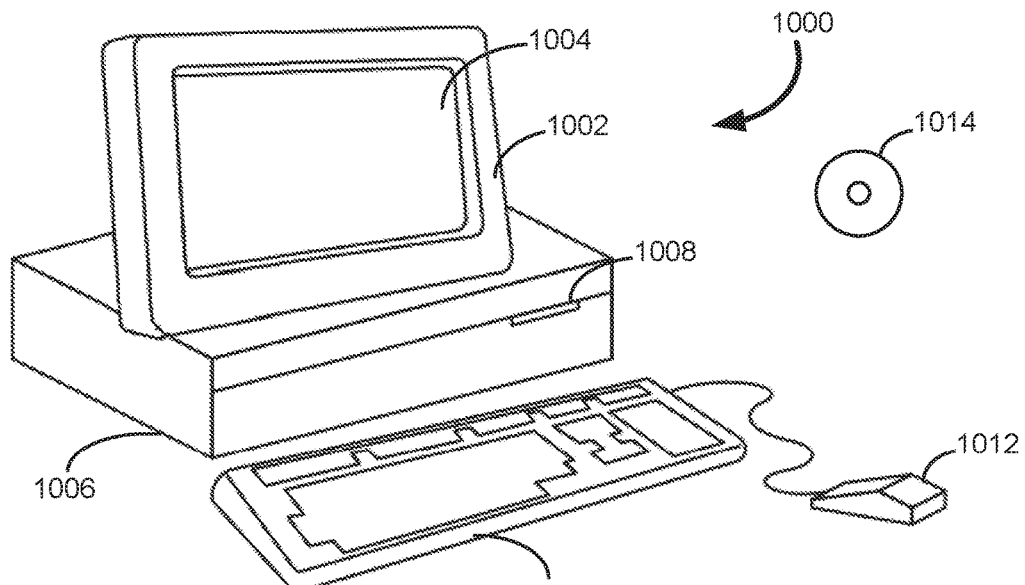
FIGS. 10A and 10B are example computer systems capable of implementing the system for automated classification generation, in accordance with some embodiments.
Figure 10B:
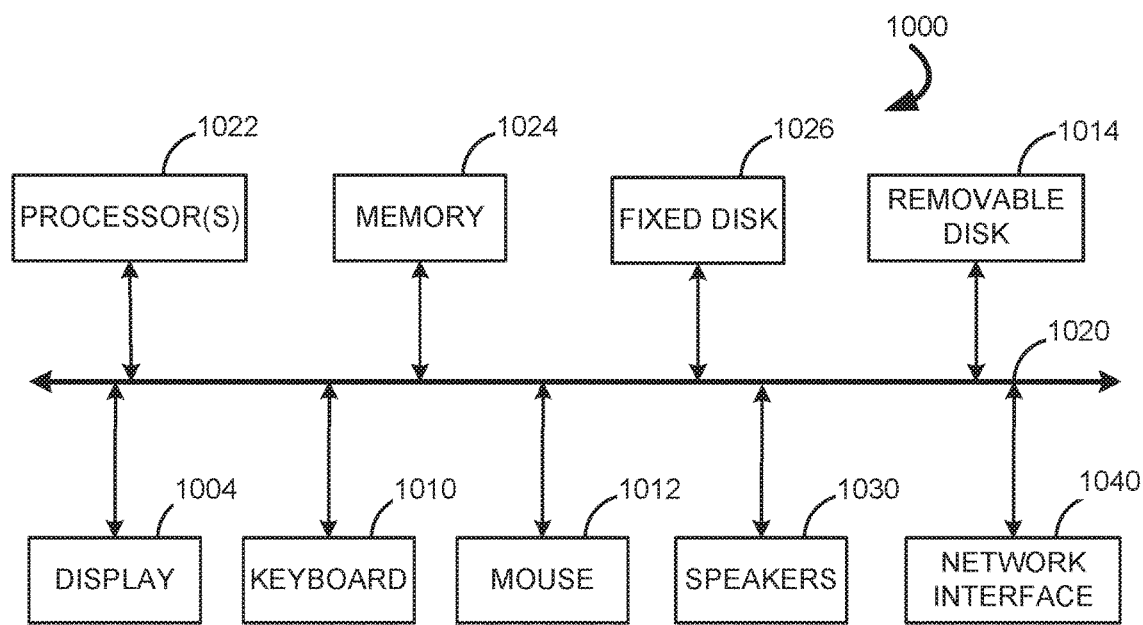

Now that the systems and methods for the autofocus OCR of medical records have been described, attention shall now be focused upon systems capable of executing the above functions. To facilitate this discussion, FIGS. 10A and 10B illustrate a Computer System 1000, which is suitable for implementing embodiments of the present invention. FIG. 10A shows one possible physical form of the Computer System 1000. Of course, the Computer System 1000 may have many physical forms ranging from a printed circuit board, an integrated circuit, and a small handheld device up to a huge super computer. Computer system 1000 may include a Monitor 1002, a Display 1004, a Housing 1006, a Disk Drive 1008, a Keyboard 1010, and a Mouse 1012. Disk 1014 is a computer-readable medium used to transfer data to and from Computer System 1000.

FIG. 10B is an example of a block diagram for Computer System 1000. Attached to System Bus 1020 are a wide variety of subsystems. Processor(s) 1022 (also referred to as central processing units, or CPUs) are coupled to storage devices, including Memory 1024. Memory 1024 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A Fixed Disk 1026 may also be coupled bi-directionally to the Processor 1022; it provides additional data storage capacity and may also include any of the computer-readable media described below. Fixed Disk 1026 may be used to store programs, data, and the like and is typically a secondary storage medium (such as a hard disk) that is slower than primary storage. It will be appreciated that the information retained within Fixed Disk 1026 may, in appropriate cases, be incorporated in standard fashion as virtual memory in Memory 1024. Removable Disk 1014 may take the form of any of the computer-readable media described below.

Processor 1022 is also coupled to a variety of input/output devices, such as Display 1004, Keyboard 1010, Mouse 1012 and Speakers 1030. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, motion sensors, brain wave readers, or other computers. Processor 1022 optionally may be coupled to another computer or telecommunications network using Network Interface 1040. With such a Network Interface 1040, it is contemplated that the Processor 1022 might receive information from the network, or might output information to the network in the course of performing the above-described autofocus OCR. Furthermore, method embodiments of the present invention may execute solely upon Processor 1022 or may execute over a network such as the Internet in conjunction with a remote CPU that shares a portion of the processing.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this disclosure. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium." A processor is considered to be "configured to execute a program" when at least one value associated with the program is stored in a register readable by the processor.

In operation, the computer system 1000 can be controlled by operating system software that includes a file management system, such as a disk operating system. One example of operating system software with associated file management system software is the family of operating systems known as Windows® from Microsoft Corporation of Redmond, Washington, and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is, here and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure may be implemented as part of an operating system or a specific application, component, program, object, module or sequence of instructions referred to as "computer programs." The computer programs typically comprise one or more instructions set at various times in various memory and storage devices in a computer, and when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention. It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer device for generating machine readable documents comprising at least one processor in communication with at least one memory device, wherein the at least one processor is programmed to:
   receive an image segmented into multiple continuous portions;
   select a first optical image recognition (OCR) transform from a plurality of OCR transforms;
   for each of the continuous portions, perform an initial OCR on the image to identify text information using the selected first OCR transform;
   for each of the continuous portions, measure an OCR signal quality of the initial OCR, wherein the signal quality measurements include at least one of a calculated figure of merit equation between characters in identified text information and an example font and maximizing entropy within identified text information area in a linear model to analyze each of the continuous portions;
   for each of the continuous portions, when the OCR signal quality of the initial OCR of a corresponding continuous portion is sufficient, output the text information of the initial OCR for the corresponding continuous portion; and
   when the OCR signal quality of the initial OCR is insufficient, the at least one processor is further programmed to:
      select a second OCR transform from remaining of the plurality of OCR transforms to perform a second OCR to identify a text information on the corresponding continuous portion;
      measure a signal quality of the second OCR on the corresponding continuous portion; and
      if the signal quality of the second OCR of the corresponding continuous portion is sufficient, output the text information from the second OCR of the corresponding continuous portion.

2. The computer device of claim 1, wherein the plurality of OCR transforms include one or more of a font matching OCR transform, a cryptogram solving OCR, and a statistical machine translation OCR.

3. The computer device of claim 1, wherein when the OCR signal quality of each of the continuous portions is sufficient, the at least one processor is further programmed to combine the continuous portions into a single document to output.

4. The computer device of claim 1, wherein for each of the continuous portions and when the OCR signal quality of the first OCR and the OCR signal quality of the second OCR are insufficient, the at least one processor is further programmed to:
   iteratively apply an additional OCR transform to the portion with insufficient OCR signal quality, wherein the additional OCR transform is different from the first OCR transform and the second OCR transform; and
   measure the OCR signal quality of the continuous portion until a sufficient OCR signal quality for the continuous portion is reached.

5. The computer device of claim 1, wherein the at least one processor is further programmed to process the image to determine which OCR transform to use as the first OCR transform.

6. The computer device of claim 1, wherein the OCR signal quality for a first continuous portion of the continuous portions is sufficient based on the first OCR transform and the OCR signal quality for a second continuous portion of the continuous portions is sufficient based on the second OCR transform, wherein the first continuous portion and the second continuous portion are different.

7. The computer device of claim 1, wherein the OCR signal quality is determined by OCR accuracy measures.

8. The computer device of claim 1, wherein the at least one processor is further programmed to identify regions of continuous OCR signal quality within the OCR image.

9. The computer device of claim 1, wherein the at least one processor is further programmed to:
   identify the OCR transform for each region of contiguous signal that has the highest OCR quality signal;
   apply the identified transform to each corresponding region of continuous signal to generate a plurality of OCR portions;

recompile the plurality of OCR portions into a single document; and
output the single document.

10. A computerized method for generating machine readable documents implemented by a computer device comprising at least one processor in communication with at least one memory device, wherein the method comprising:
receiving an image segmented into multiple continuous portions;
selecting a first optical image recognition (OCR) transform from a plurality of OCR transforms comprising;
for each of the continuous portions, performing an initial OCR on the image to identify text information using the selected first OCR transform;
for each of the continuous portions, measuring an OCR signal quality of the initial OCR, wherein the signal quality measurements include at least one of a calculated figure of merit equation between characters in identified text information and an example font and maximizing entropy within identified text information area in a linear model to analyze each of the continuous portions;
for each of the continuous portions, when the OCR signal quality of the initial OCR of a corresponding continuous portion is sufficient, outputting the text information of the initial OCR for the corresponding continuous portion; and
when the OCR signal quality of the initial OCR is insufficient, the method further comprises:
selecting a second OCR transform from remaining of the plurality of OCR transforms to perform a second OCR to identify a text information on the corresponding continuous portion;
measuring a signal quality of the second OCR on the corresponding continuous portion; and
if the signal quality of the second OCR of the corresponding continuous portion is sufficient, outputting the text information from the second OCR for the corresponding continuous portion.

11. The method of claim 10, wherein the plurality of OCR transforms include one or more of a font matching OCR transform, a cryptogram solving OCR, and a statistical machine translation OCR.

12. The method of claim 10, wherein when the OCR signal quality of each of the continuous portions is sufficient, the method further comprises combining the continuous portions into a single document to output.

13. The method of claim 10, wherein for each of the continuous portions and when the OCR signal quality of the first OCR and the OCR signal quality of the second OCR are insufficient, the method further comprises:
iteratively applying an additional OCR transform to the portion with insufficient OCR signal quality, wherein the additional OCR transform is different from the first OCR transform and the second OCR transform; and
measuring the OCR signal quality of the continuous portion until a sufficient OCR signal quality for the continuous portion is reached.

14. The method of claim 10 further comprises processing the image to determine which OCR transform to use as the first OCR transform.

15. The method of claim 10, wherein the first OCR transform is at least one of a font matching OCR transform, a cryptogram solving OCR, and a statistical machine translation OCR, wherein the second OCR transform is at least one of the font matching OCR transform, the cryptogram solving OCR, and the statistical machine translation OCR, and wherein the first OCR transform and the second OCR transform are different.

16. The method of claim 10, wherein the OCR signal quality is determined by OCR accuracy measures.

17. The method of claim 10, further comprising identifying regions of continuous OCR signal quality within the OCR image.

18. The method of claim 10 further comprising:
identifying the OCR transform for each region of contiguous signal that has the highest OCR quality signal;
applying the identified transform to each corresponding region of continuous signal to generate a plurality of OCR portions;
recompiling the plurality of OCR portions into a single document; and
outputting the single document.

* * * * *